United States Patent [19]

Sebag et al.

[11] Patent Number: 4,963,535
[45] Date of Patent: Oct. 16, 1990

[54] NONIRRITANT COSMETIC COMPOSITIONS CONTAINING A FOAMING SURFACTANT AND A NONIONIC SURFACTANT CONTAINING TWO FATTY CHAINS

[75] Inventors: Henri Sebag, Paris; Guy Vanlerberghe, Claye-Souilly, both of France

[73] Assignee: L'Oreal, Paris, France

[21] Appl. No.: 151,462

[22] Filed: Feb. 2, 1988

[30] Foreign Application Priority Data

Feb. 3, 1987 [LU] Luxembourg .................. 86756

[51] Int. Cl.$^5$ .................. A61K 7/42; A61K 7/06
[52] U.S. Cl. .................. 514/54; 514/845; 514/846; 514/847; 514/941; 424/47; 424/70; 568/27; 568/45; 568/46; 568/50; 568/59; 568/614; 568/616; 568/623; 252/DIG. 1; 252/DIG. 5; 252/DIG. 13; 252/DIG. 14
[58] Field of Search .................. 514/54, 845, 846, 847, 514/941; 424/47, 70; 568/27, 45, 46, 50, 59, 614, 616, 623; 252/DIG. 1, DIG. 5, DIG. 14, DIG. 13

[56] References Cited

U.S. PATENT DOCUMENTS

| 4,001,141 | 1/1977 | Kalopissis et al. .................. 252/309 |
| 4,491,534 | 1/1985 | Vanlerberghe et al. .................. 252/357 |
| 4,532,125 | 7/1985 | Vanlerberghe et al. .................. 536/116 |
| 4,620,037 | 10/1986 | Vanlerberghe et al. .................. 568/36 |
| 4,666,711 | 5/1987 | Vanlerberghe et al. .................. 514/845 |

FOREIGN PATENT DOCUMENTS

| 2017240 | 5/1970 | France . |
| 2401187 | 3/1979 | France . |
| 2452506 | 10/1980 | France . |
| 518249 | 3/1972 | Switzerland . |

Primary Examiner—Ronald W. Griffin
Attorney, Agent, or Firm—Cushman, Darby & Cushman

[57] ABSTRACT

Cosmetic compositions for cleaning hair, the skin or for removing make-up from the face or from the eyes, containing (a) a foaming surface-active agent, (b) an aqueous, hydroalcoholic or oily carrier and (c) a nonfoaming, nonionic product, poorly soluble in water, of general formula (I):

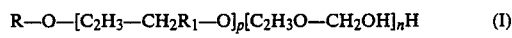

$$R-O-[C_2H_3-CH_2R_1-O]_p[C_2H_3O-CH_2OH]_nH \qquad (I)$$

in which R denotes a $C_8$–$C_{20}$ alkyl radical, $R_1$ denotes a $C_7$–$C_{17}$ alkyl radical or an alkoxy radical containing from 8 to 20 carbon atoms, $R+R_1$ containing from 21 to 31 carbon atoms and preferably from 23 to 27, p denotes the exact value of $\underline{1}$ or a statistical mean value of between 1 and 2, and $\overline{n}$ denotes a statistical mean value of between 2 and 10 and preferably between 2.5 and 7.

The presence of the component (c) improves the compatibility of the foaming surface-active agents (a) with the skin and the mucosa.

11 Claims, No Drawings

NONIRRITANT COSMETIC COMPOSITIONS CONTAINING A FOAMING SURFACTANT AND A NONIONIC SURFACTANT CONTAINING TWO FATTY CHAINS

The invention relates to new nonirritant, surface-active cosmetic compositions which may be employed more particularly as shampoos or as lotions for cleaning the body and the face or as lotions for removing make-up, especially in the case of eyes.

One of the factors which limit the use of care compositions in cosmetics and more particularly in the case of shampoos and compositions for removing make-up, is the irritancy of the surfactants which they contain towards the skin and towards the mucosa and in particular towards mucosa of the eyes.

This irritancy can be evaluated by various tests in vitro or on animals, especially by the official Draize test which makes it possible to follow the effect of a product on the rabbit's eye from the instillation and over several days, or by the reduction in the toxicity towards cells such as red blood corpuscles.

The Draize test is described, inter alia, in the article by J. H. Draize and Elsie A. Kelley in the Proceedings of Scientific Section T.G.A. No. 17, May 1952.

The irritancy of the surfactants depends on their structure, particularly on the chemical class, on the length of the hydrocarbon chain and on the nature of the hydrophilic group.

Frequently, however, the compounds which are tolerated best are not the best foamers and in many cases the products chosen represent compromises between the physicochemical and practical properties and biological properties.

It is known, for example, that lengthening of the hydrocarbon chain from 12 to 18 carbon atoms makes it possible to obtain products which are less irritant towards eye mucosa, but the products containing a longer hydrocarbon chain exhibit less satisfactory foaming properties and, furthermore, exhibit crystallization phenomena (Kraft point) in the case of the linear hydrocarbon chains. This is particularly the case with anionic surfactants.

Furthermore, insofar as nonionic surfactants are concerned, the irritancy depends, in addition, on the nature and on the length of the hydrophilic group. Thus, in the case of polyoxyethylenated nonionic surfactants of a given fatty chain length, it is observed that the foaming capacity passes through an optimum as a function of the number of ethyleneoxy units and that the irritancy gradually diminishes when this number of ethyleneoxy units increases.

In a number of cases, there is a need to reduce the irritancy of the cosmetic compositions which are satisfactory from the standpoint of the foaming properties.

It has been found that the addition of nonionic surface-active products of formula (I) shown below has the effect of markedly reducing the irritancy of the foaming compositions in which they are present, without a marked decrease in the foaming properties.

It is surprising and unexpected to find that the addition of nonionic products which are poorly soluble in water or even liposoluble, and nonfoaming, to foaming compositions, in proportions of between 5% and 50% by weight relative to the weight of the foaming surfactant(s) present in the cosmetic compositions, permits an appreciable reduction in the irritancy particularly to the eyes without markedly reducing the foaming properties.

The subject of the invention is therefore a foaming cosmetic composition capable of being employed for the cleaning and for the care of hair and of the skin, containing nonionic, nonfoaming surface-active products, containing two fatty chains, of formula (I), which products are associated with foaming surfactants which may be anionic, nonionic, amphoteric, zwitterionic or cationic, as well as mixtures thereof.

The nonfoaming nonionic surface-active products containing two fatty chains of formula (I) have the general formula:

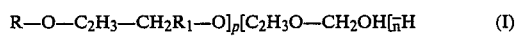

in which:

R denotes a $C_8$–$C_{20}$ alkyl radical, $R_1$ denotes a $C_7$–$C_{17}$ alkyl radical or an alkoxy radical containing from 8 to 20 carbon atoms, R+$R_1$ containing from 21 to 31 carbon atoms and preferably from 23 to 27, p denotes the exact value of 1 or a statistical mean value of between 1 and 2, and $\bar{n}$ denotes a statistical mean value of between 2 and 10 and preferably between 2.5 and 7.

In the above formula, the unit

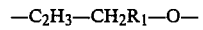

denotes the two isomers

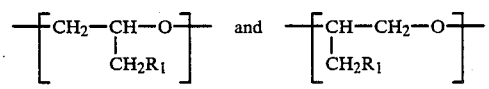

and the unit

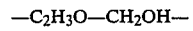

denotes the two isomers

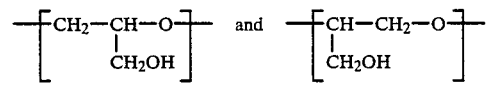

The formula (I) denotes a mixture of nonionic compounds which may be prepared in a manner which is known per se.

The process of preparation consists in preparing compounds of formula II:

by reacting an epoxide of formula:

with an alcohol ROH, R and $R_1$ having the meanings indicated above, in the presence of an acidic catalyst within the Lewis meaning, at a temperature of between 20° and 120° C. or in the presence of a basic catalyst at a temperature of between 100° and 180° C.

The compound of formula III is generally employed in proportions of 0.2/1 to 1.8/1 relative to the alcohol ROH. The alcohol ROH which may be present at the end of the reaction is removed by heating under reduced pressure. This alcohol may be present either because of the fact that it has been employed in excess, or because it has not been completely consumed in the reaction.

When the reaction is carried out with a large excess of alcohol ROH relative to the epoxide III, then, after removal of the uncondensed alcohol, a product II is obtained, consisting essentially of a compound in which p denotes the value 1.

When the alcohol ROH is employed in a slight excess and, even more so, in deficiency relative to the epoxide, a mixture of products of formula II is obtained, where p has a statistical mean value of between 1 and 2. After removal of any alcohol ROH which may be present, the reaction product may be employed either as such, without further purification, for the preparation of the products of formula (I), or may be purified by distillation to isolate the compound II in which p=1, as described in French Pat. No. 2,465,780.

The compounds of formula (II) are converted into compounds of formula (I) by following conventional procedures, either by polyaddition of n mols of epihalohydrin with one mol of alcohol of formula (II), followed by a hydroxylation,-or by polyaddition of n mols of tertbutyl glycidyl ether with one mol of alcohol of formula (II), followed by a scission of the tert-butoxy group. These procedures are described in greater detail in French Pat. No. 2,465,780 and U.S. Pat. No. 4,666,711. The nonionic products of general formula (I) in which p=1, are also described in French Pat. No. 2,465,780 and in U.S. Pat. No. 4,666,711.

The nonionic products of general formula (I) in which p denotes a statistical mean value of between 1 and 2 are new.

Another subject of the invention is the new compounds of formula (I) in which p denotes a statistical mean value of between 1 and 2, R, $R_1$ and n having the meanings indicated above.

The nonionic products of formula (I) are generally very viscous liquids or pastes, which are partially or completely soluble in oils and poorly soluble in water.

They present the advantage of reducing the irritancy of the foaming surface-active compounds with which they are associated. This reduction can be demonstrated using the Draize test. It is especially marked a few days after the instillation, with a more rapid return of the mucosa to the normal state.

The reduction in the irritancy of a solution of surface-active compounds can also be demonstrated in respect of cells such as red blood cells.

The nonionic products of formula (I) are employed in proportions from 5 to 50% by weight, and preferably from 10 to 30% by weight relative to the foaming surfactant(s).

The cosmetic compositions according to the invention are characterized in that they contain a foaming surface-active agent (a) chosen from anionic, nonionic, amphoteric, zwitterionic and cationic surfactants and mixtures thereof, a carrier (b) chosen from water, mixtures of water with a monoalcohol containing 1 to 4 carbon atoms and vegetable, mineral and animal oils, the irritancy of this composition towards the skin and the mucosa being reduced by the presence in the composition of a mixture (c) of nonfoaming, nonionic products of general formula (I), the weight ratio c:a being between 5:100 and 50:100 and preferably between 10:100 and 30:100.

Among the anionic surface-active agents (a) there may be mentioned sodium, potassium, ammonium and alkanolamine alkyl sulphates, sodium, potassium, ammonium and alkanolamine alkyl ether sulphates, alkylbenzenesulphonates, olefinsulphonates and alkylsulphonates, soaps, acylisethionates, N-acyltaurines, N-acylsarcosinates and salts of alkoxypolyethoxymethylcarboxylic acids; the alkyl or alkenyl radicals in the abovementioned compounds contain from 10 to 18 carbon atoms.

Among the preferred nonionic surfactants there may be mentioned polyglycerol ethers, polyoxyethylenated ($C_8$–$C_{18}$) alcohols, polyoxyethylenated ($C_8$–$C_{12}$)-alkylphenols and ($C_8$–$C_{18}$)-alkylpolyglycosides.

Among the polyglycerol ethers there may be mentioned:

the compounds of formula:

$$R_2O-C_2H_3O\ (CH_2OH]n_2H \qquad (V)$$

where $R_2$ is a linear or branched $C_8$–$C_{22}$ alkyl or alkenyl radical, an alkylaryl radical containing a linear or branched $C_8$–$C_{12}$ alkyl chain, or else a hydrocarbon radical derived from aliphatic or alicyclic alcohols of natural or synthetic origin, containing up to 30 carbon atoms, $n_2$ being a number equal to or smaller than 10. These compounds are described in French Pat. No. 1,477,048 and its Certificate of Addition No. 94,928 and in U.S. Pat. No. 3,578,719, and the compounds of formula:

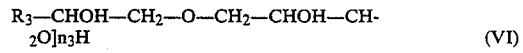

$$R_3-CHOH-CH_2-O-CH_2-CHOH-CH_2O]n_3H \qquad (VI)$$

where $R_3$ denotes an aliphatic, cycloaliphatic or arylaliphatic radical containing from 7 to 21 carbon atoms, it being possible for the aliphatic chains to be saturated or unsaturated, linear or branched and to contain ether, thioether and/or hydroxymethylene groups; $n_3$ is an integer or decimal greater than 1 and equal to or smaller than 10 and denotes the average degree of polymerization. These compounds may be prepared according to the procedures described in French Pat. No. 2,091,516 or in the French Patent Application published under No. 2,574,786.

Among the alkyl- and hydroxyalkylpolyglycosides there should be mentioned those in which the alkyl radical contains from 8 to 18 carbon atoms and in which the number of glycoside units is between 1 and 25. Among these compounds, there may be mentioned Triton CG 110, sold by SEPPIC.

The procedure for preparing alkylpolyglycosides is described in French Pat. No. 2,017,240. The procedure for preparing hydroxyalkylpolyglycosides is described in French Pat. No. 2,397,185.

Among the amphoteric or zwitterionic foaming surfactants there may be mentioned ($C_{12}$–$C_{18}$) alkyl- and alkenylimidazolines such as the product sold under the name of Miranol C 2 M and referred to under the name "cocoamphocarboxypropionate" in the Cosmetic Ingredient Dictionary, 3rd edition, published by The Cosmetic Toiletry and Fragrance Association (called briefly the CTFA dictionary), N-($C_{10}$–$C_{18}$)-alkylbetaines such as N-alkyl(copra)dimethylcarboxymethylammonium, sold under the name Dehyton AB 30 and referred to under the name "cocobetaine" in the CFTA dictionary, N-($C_{10}$–$C_{18}$)-alkylamidoalkyl-betaines, such as, for example, alkyl(copra)amidopropylbetaine sold under the name Tegobetaine L7 by Goldschmidt and referred to under the name "cocamido-propyl betaine" in the CTFA dictionary.

Among the cationic foaming surfactants there may be mentioned trimethyl ($C_{12}$–$C_{18}$)-alkylammonium halides, dimethyldi($C_{12}$–$C_{18}$)-alkylammonium halides and dimethylhydroxyethylcetylammonium chloride.

The cosmetic compositions for cleaning hair or the skin or for removing make-up from the eyes according to the invention may also contain adjuvants which are usually employed in cosmetic compositions, especially anionic, cationic, nonionic or amphoteric polymers or resins, thickeners, opacifiers, foam synergists, foam stabilizers, preserving agents, perfumes or pH modifiers. They may also contain propellants and may be presented in aerosol form.

As thickeners which may be employed there may be mentioned particularly cellulose derivatives such as carboxymethyl cellulose, hydroxypropyl methyl cellulose, hydroxyethyl cellulose and acrylic polymers. The thickeners are generally employed in a proportion of 0.1 to 20% of the total weight of the composition.

Among the foam stabilizers there should be mentioned more particularly alkanolamides, especially copra diethanolamide, 1,2-alkanediols such as 1,2-dodecanediol, employed in a proportion of 1 to 10% by weight of the total weight of the composition.

As oils which serve as a carrier, use may be made of mineral, vegetable or animal oils, modified or otherwise, such as liquid petrolatum, paraffin oils, almond oil, groundhut oil, rape oil, copra oil, wheatgerm oil, jojoba oil, corn oil, olive oil, palm oil, sesame oil, sunflower oil or perhydrosqualene.

A further subject of the invention is a process for cleaning hair or the skin or for removing make-up from eyes, consisting in applying to the hair, the skin or around the eyes a quantity which is sufficient for the cleaning or the removal of make-up of a cosmetic composition containing: (a) a foaming surface-active agent chosen from anionic, nonionic, amphoteric, zwitterionic or cationic foaming surfactants and mixtures thereof, (b) a carrier chosen from water, a mixture of water with a lower $C_1$-$C_4$-alcohol and oils of animal, vegetable or mineral origin, characterized in that it additionally contains a mixture (c) of nonfoaming, nonionic products which are poorly soluble in water of general formula (I) where R, $R_1$ and n have the above meanings, p denotes the exact value 1 or a statistical mean value of between 1 and 2, the weight ratio c:a being between 5:100 and 50:100.

A further subject of the invention is a process for reducing the irritancy of foaming surfactants towards the skin and towards mucosa of the eye, by addition of 5 to 50% by weight of nonionic compounds of formula (I) relative to the foaming surfactant(s) present in the composition.

The invention will be understood better with the aid of the following examples which do not imply any limitation:

EXAMPLES OF PREPARATION

EXAMPLE 1

Preparation of a mixture of compounds of formula (I) in which:

$R = C_{12}H_{25}$ $R_1$ = mixture of $C_{13}$ and $C_{15}$ alkyl radicals
$p = 1.16$
$n = 3$.

(a) Preparation of the mixture of alcohols of formula:

$$R-O-C_2H_3-CH_2R_1-O]_pH \quad (II)$$

2.7 g of sodium methylate in methanol (0.015 mole) are added to 167.4 g (0.9 mole) of molten 1-dodecanol. Heating is applied, under a stream of nitrogen, up to 150° C., while the methanol formed is removed, and a mixture of 36 g (0.15 mole) of 1,2-epoxyhexadecane and 40.2 g (0.15 mole) of 1,2-epoxyoctadecane is then added over a period of approximately 1 hour 15 minutes. The temperature and the stirring are maintained for approximately 4 hours. Determinations are carried out to check that all the epoxide has reacted.

The reaction mixture is washed twice with an equivalent weight of boiling water. 1.3 ml of concentrated hydrochloric acid is introduced during the first washing. After drying, 119 g of excess 1-dodecanol are distilled off by heating under reduced pressure.

The residual mass corresponds to a mixture of alcohols of general formula (II) in which p denotes a statistical mean value of 1.16.

(b) Preparation of the mixture of products of formula (I):

$$R-O-C_2H_3(CH_2R_1)O]_p[C_2H_3O\ (CH_2OH)]_nH \quad (I)$$

where R, $R_1$, n and p have the values shown above.

3 moles of epichlorohydrin are added to the alcohol of formula (II) obtained in step (a) the polyhalogenated compound being then subjected to a hydroxylation according to the process described in French Pat. No. 2,465,780 and in U.S. Pat. No. 4,666,711.

EXAMPLE 2

Preparation of a mixture of compounds of formula (I) in which:

$R = C_{12}H_{25}$
$R_1$ = a mixture of $C_{13}$ and $C_{15}$ alkyl radicals
$n = 7$
$p = 1.16$ This mixture of compounds is prepared similarly to that in Example 1.

The mixture of compounds 3 to 5 below are prepared according to the procedure described in French Pat. No. 2,465,780 and in U.S. Pat. No. 4,666,711.

Mixture of compounds 3—prepared according to Example 8A of French Pat. No. 2,465,780 and of U.S. Pat. No. 4,666,711
$R = C_8H_{17}$
$R_1 = C_{15}H_{31}$
p = exact value of 1
n = 3

Mixture of compounds 4—prepared according to Example 11A of French Pat. No. 2,465,780 and of U.S. Pat. No. 4,666,711
$R = C_{12}H_{25}$
$R_1 = C_{11}H_{23}$
p = exact value of 1
n = 5

Mixtures of compounds 5—prepared according to Example 3A of French Pat. No. 2,465,780 and of U.S. Pat. No. 4,666,711
R=C$_{16}$H$_{33}$

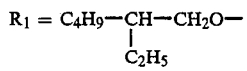

p=exact value of 1
n=3

EXAMPLES OF COSMETIC CLEANING COMPOSITIONS

EXAMPLE A1

| Foaming washing oil | |
|---|---|
| Mixture of compounds No. 1 | 3 g |
| Mixture of monoisopropanolamine lauryl ether sulphate and of copra diethanolamides, sold under the name Texapon WW99 by Henkel | 30 g |
| Liquid petrolatum | 28 g |
| Perfume, preservative, q.s. (sufficient quantity) | |
| Rape oil | q s. 100 g |

EXAMPLE A2

| Foaming washing oil | |
|---|---|
| Mixture of compounds No. 1 | 1.5 g |
| Mixture of monoisopropanolamine lauryl ether sulphate and of copra diethanolamides, sold under the name Texapon WW99 by Henkel | 30 g |
| Liquid petrolatum | 28 g |
| Groundnut oil | q s. 100 g |

EXAMPLE A3

| Anionic shampoo | |
|---|---|
| Mixture of compounds No. 3 | 1.5 g |
| Sodium lauryl ether sulphate | 6.25 g |
| Copra diethanolamides | 4 g |
| Ethylenediaminetetraacetic acid | 0.2 g |
| HCl q.s. pH 7.4 | |
| Water | q.s. 100 g |

EXAMPLE A4

| Shampoo (anionic + amphoteric) | |
|---|---|
| Mixture of compounds No. 1 | 2 g |
| Ammonium lauryl sulphate | 7.5 g |
| Carboxymethylalkyl(copra)dimethylammonium, sold under the name of Dehyton AB 30 by Henkel | 1.2 g |
| Copra diethanolamides | 2 g |
| Water | q.s. 100 g |
| pH = 7.1 | |

EXAMPLE A5

| Shampoo (anionic + amphoteric) | |
|---|---|
| Mixture of compounds No. 1 | 2.5 g |
| Sodium lauryl ether sulphate | 2.5 g |

| Shampoo (anionic + amphoteric) | |
|---|---|
| Cocoamphocarboxypropionate (amphoteric surfactant) sold under the name Miranol C2M by Miranol | 8 9 |
| Copra diethanolamides | 4 g |
| Quaternary copolymer of vinylpyrrolidone and of dimethylaminoethyl methacrylate (80:20), MW of approximately 1,000,000, sold under the name of Gafquat 755 by GAF | 1 g |
| HCl q.s. pH 7.5 | |
| Water | q.s. 100 g |

EXAMPLE A6

| Shampoo (anionic + nonionic) | |
|---|---|
| Mixture of compounds No. 3 | 2 g |
| Polyglycerol lauryl ether containing 4 moles of glycerol | 6 g |
| Sodium alkyl ether sulphate sold under the name Texapon ASV by Henkel | 5.4 g |
| NaOH q.s. pH 7 | |
| Water | q.s. 100 g |

EXAMPLE A7

| Shampoo (nonionic) | |
|---|---|
| Mixture of compounds No. 3 | 3 g |
| Ethers of 1,2-dodecanediol and of polyglycerols containing 3.9 moles of glycerol (prepared according to Example 3 of U.S. Pat. No. 4,666,711 and of French Patent 2,574,780 | 5 g |
| Glucoside alkyl ether sold under the name Triton CG 110-60 by SEPPIC | 5.4 g |
| Copolymer of dimethyldiallylammonium chloride and of acrylamide with a molecular weight of approximatly 500,000 and sold under the name of Merquat 550 by Merck | 0.6 g |
| NaOH q.s. pH 7 | |
| Water | q.s. 100 g |

EXAMPLE A8

| Shampoo (nonionic) | |
|---|---|
| Mixture of compounds No. 3 | 2.5 g |
| Polyethylene glycol (C$_{12}$-C$_{14}$)-alkyl ether oxyethylenated with 12 moles of ethylene oxide | 12 g |
| Dimethyldistearylammonium chloride | 0.2 g |
| NaOH q.s. pH 6.9 | |
| Water | q.s. 100 g |

EXAMPLE A9

| Body-cleaning liquid | |
|---|---|
| Mixture of compounds of Example 1 | 2 g |
| Ethers of 1,2-dodecanediol and of polyglycerols containing 3.9 moles of glycerol, prepared according to Example 3 of French Patent 2,574,780 and of U.S. Pat. No. 4,666,711 | 9 g |
| Copolymer of ethylene oxide and of propylene oxide, sold under the name Pluronic L62 by BASF Wyandotte | 9 g |
| | 4 g |
| Water | q.s. 100 g |

EXAMPLE A10

| Nonionic surfactant of formula: R—CHOH—CH$_2$—O—[CH$_2$—CHOH—CH$_2$—O]$_{\overline{3.5}}$H R = C$_{10}$H$_{21}$ | 1 g |
|---|---|
| Mixture of compounds No. 3 | 0.3 g |
| Hexylene glycol | 1 g |
| Potassium dihydrogen phosphate | 0.1 g |
| Potassium hydrogen phosphate | 0.3 g |
| Allantoin | 0.05 g |
| Merthiolate | 0.003 g |
| Perfume q.s. | |
| Sterile demineralized water | q.s. 100 g |

EXAMPLE A11

| Cleaning foam for the face | |
|---|---|
| Potassium lauryl sulphate | 10 g |
| Mixture of compounds No. 1 | 2 g |
| Glycerine | 5 g |
| Preservative q.s. | |
| Perfume | 0.3 g |
| Sterile demineralized water | q.s. 100 g |

EXAMPLE A12

| Antiseptic cleaning gel for skins affected by acne | |
|---|---|
| Trimethylcetylammonium bromide, sold under the name Cetrimide | 5 g |
| Mixture of compounds No. 2 | 1.5 g |
| Hydroxyethyl cellulose | 1 g |
| Propylene glycol | 3 g |
| Preservative q.s. | |
| Perfume q.s. | |
| Sterile demineralized water | q.s. 100 g |

We claim:

1. A cosmetic composition for cleansing hair or the skin or removing make-up from the eyes, said composition comprising
    (a) at least one foaming surface-active agent selected from the group consisting of an anionic, nonionic, amphoteric, zwitterionic and cationic foaming surfactant and a mixture thereof,
    (b) a carrier selected from the group consisting of water; a mixture of water and a C$_1$–C$_4$ lower alcohol; and an oil selected from the group consisting of a vegetable oil, a mineral oil and an animal oil and
    (c) a nonfoaming, nonionic product having the formula:

$$R-O-C_2H_3-(CH_2R_1-O]_pC_2H_3O-CH_2OH)]_{\overline{n}}H \quad (I)$$

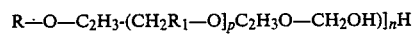

wherein
    R represents a C$_8$–C$_{20}$ alkyl radical,
    R$_1$ represents a C$_7$–C$_{17}$ alkyl radical or a C$_8$–C$_{20}$ alkoxy radical,
    R+R$_1$ contain from 21 to 31 carbon atoms,
    p represents the exact value of 1 or a statistical means value between 1 and 2, and
    $\overline{n}$ represents a statistical means value of between 2 and 10,
the weight ratio c:a being between 5:100 and 50:100.

2. The cosmetic composition of claim 1 wherein R+R$_1$ contain from 23 to 27 carbon atoms.

3. The cosmetic composition of claim 1 wherein $\overline{n}$ represents a statistical means value between 2.5 and 7.

4. The cosmetic composition of claim 1 wherein the weight ration c:a between 10:100 and 30:100.

5. The cosmetic composition of claim 1 wherein said foaming surface-active agent (a) is selected from the group consisting of
    (i) an anionic surfactant selected from the group consisting of sodium, potassium, ammonium and alkanolamine alkyl suphate; sodium, potassium, ammonium and alkanolamine alkyl ether sulphate; alkylbenzenesulphonate; alkenylsulphonate; alkylsulphonate; soap; acylisethionate; N-acyltaurine; N-acylsarcosinate; and a salt of an alkoxypolyethoxymethylcarboxylic acid; wherein the alkyl and alkenyl moieties contain from 10 to 18 carbon atoms;
    (ii) a nonionic surfactant selected from the group consisting of a polyglycerol ether; a polyoxyethylenated (C$_8$–C$_{18}$) alcohol; a polyoxyethylenated (C$_8$–C$_{12}$) alkylphenol; and a (C$_8$–C$_{18}$)-alkyl (poly) glycoside;
    (iii) an amphoteric or zwitterionic surfactant selected from the group consisting of a (C$_{12}$–C$_{18}$)-alkylimidazoline; a (C$_{12}$–C$_{18}$)-alkenylimidazoline; an N-(C$_{10}$–C$_{18}$)-alkylbetaine; and an N-(C$_{10}$–C$_{18}$)-alkylamidoalkylbetaine; and
    (iv) a cationic surfactant selected from the group consisting of a trimethyl (C$_{12}$–C$_{18}$) alkylammonium halide; a dimethyldi (C$_{12}$–C$_{18}$)-alkylammonium halide; and dimethylhydroxyethylcetylammonium chloride.

6. The cosmetic composition of claim 1 in the form of an aqueous or hydraalcoholic solution, an aqueous or hydraalcoholic gel, an oily solution or packaged as an aerosol.

7. The cosmetic composition of claim 1 wherein said carrier (b) is an oil, modified or not, selected from the group consisting of almond oil, groundout oil, rape oil, copra oil, wheatgerm oil, jojoba oil, olive oil, palm oil, sesame oil, sunflower oil, paraffin oil, liquid petroleum and perhydrosqualene.

8. The cosmetic composition of claim 1 which also includes at least one adjuvant selected from the group consisting of an anionic, cationic, nonionic or amphoteric resin or polymer; a thickener; an opacifier; a foam synergist; a foam stabilizer; a preserving agent, a perfume and pH modifier.

9. A process for reducing the irratancy of a foaming surface-active agent towards the skin or towards the mucosa of the eye comprising combining with said foaming surface-active agent, in an amount ranging from 5 to 50 percent by weight based on the weight of said foaming surface-active agent, a compound having the formula $$R-O-C_2H_3-(CH_2R_1-O]_pC_2H_3OH)]_{\overline{n}}H \quad (I)$$

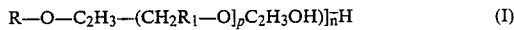

wherein
    R represents a C$_8$–C$_{20}$ alkyl radical,
    R$_1$ represents a C$_7$–C$_{17}$ alkyl radical or a C$_8$–C$_{20}$ alkoxy radical,
    R+R$_1$ contain from 21 to 31 carbon atoms,
    p represents the exact amount of 1 or a statistical means value between 1 and 2, and
    $\overline{n}$ represents s statistical means value of between 2 and 10, said foaming surface-active agent and said compound being dissolved in an aqueous, hydroalcoholic or oily medium.

10. A process for cleansing hair or the skin or for removing make-up from the eyes, said process comprising applying to the hair or skin or around the eyes, in an amount effective to cleanse the hair or skin or to remove make-up from the eyes a cosmetic composition comprising
   (a) at least one foaming surface-active agent selected from the group consisting of an anionic, nonionic, amphoteric, zwitterionic and cationic foaming surfactant and a mixture thereof,
   (b) a carrier selected from the group consisting of water; a mixture of water and a $C_1$–$C_4$ lower alcohol; and an oil selected from the group consisting of a vegetable oil, a mineral oil and an animal oil and
   (c) a nonfoaming, nonionic product having the formula:

$$R-O-C_2H_3-(CH_2R_1-O)_p[C_2H_3O-CH_2OH]_{\overline{n}}H \qquad (I)$$

wherein

R represents a $C_8$–$C_{20}$ alkyl radical, $R_1$ represents a $C_7$–$C_{17}$ alkyl radical or a $C_8$–$C_{20}$ alkoxy radical, $R+R_1$ contain from 21 to 31 carbon atoms, p represents the exact value of 1 or a statistical mean value between 1 and 2, and $\overline{n}$ represents a statistical mean value of between 2 and 10, the weight ratio c:a being between 5:100 and 50:100.

11. A mixture of nonionic products having the formula $$R-O-C_2H_3-(CH_2R_1-O)_p[C_2H_3O-CH_2OH]_{\overline{n}}H \qquad (I)$$

wherein

R represents a $C_8$–$C_{20}$ alkyl radical, $R_1$ represents a $C_7$–$C_{17}$ alkyl radical or a $C_8$–$C_{20}$ alkoxy radical, $R+R_1$ contain from 21 to 31 carbon atoms, p represents a statistical means value between 1 and 2, and $\overline{n}$ represents a statistical means value of between 2 and 10.

* * * * *